(12) United States Patent
Madsen

(10) Patent No.: US 6,761,718 B2
(45) Date of Patent: Jul. 13, 2004

(54) DIRECTION-ORIENTED AND SPATIALLY CONTROLLED BIPOLAR COAGULATOR FOR IN-SITU CAUTERIZATION OF ADHERENT CRANIAL TISSUE OCCLUDING A VENTRICULAR CATHETER PREVIOUSLY IMPLANTED IN-VIVO

(75) Inventor: Joseph R. Madsen, Newton, MA (US)

(73) Assignee: Children's Medical Center Corp., Boston, MA (US)

( * ) Notice: Subject to any disclaimer, the term of this patent is extended or adjusted under 35 U.S.C. 154(b) by 86 days.

(21) Appl. No.: 09/947,707

(22) Filed: Sep. 6, 2001

(65) Prior Publication Data

US 2003/0045870 A1 Mar. 6, 2003

(51) Int. Cl.[7] ............................................... A61B 18/18

(52) U.S. Cl. ....................................................... 606/50
(58) Field of Search ............................. 606/41, 45, 46, 606/47, 48, 49, 50

(56) References Cited

U.S. PATENT DOCUMENTS 4,106,511 A * 8/1978 Erlandsson .................. 607/41

* cited by examiner

Primary Examiner—Rosiland Rollins
(74) Attorney, Agent, or Firm—David Prashker

(57) ABSTRACT

The present invention provides a bipolar coagulator which can be passed through the internal lumen of a ventricular catheter previously implanted into a cranial ventricle of a living subject and engaged in-situ. The bipolar coagulator will provide bipolar electrical arc currents for coagulation cauterization of adherent brain tissues, such as the choroid plexus, which occludes fluid flow into the intake drainage holes in the implanted ventricular catheter and often becomes adherent to the catheter in-situ. The cautery current provided by the bipolar coagulator is direction oriented and spatially controlled; thereby providing a better distribution of electrical current and heat within the surrounding cranial tissues; and thereby avoiding major complications of damage to intracranial structures such as blood vessels as well as avoiding the severe subarachnoid hemorrhages which are typical using other kinds of coagulation instruments.

8 Claims, 10 Drawing Sheets

DIRECTION-ORIENTED AND SPATIALLY CONTROLLED BIPOLAR COAGULATOR FOR IN-SITU CAUTERIZATION OF ADHERENT CRANIAL TISSUE OCCLUDING A VENTRICULAR CATHETER PREVIOUSLY IMPLANTED IN-VIVO

FIELD OF THE INVENTION

The present invention is directed generally to ventricular catheters which have been previously implanted in-vivo into one or more ventricles of the human brain for therapeutic purposes; and is particularly directed to removing adherent tissue occlusions of ventriculoperitoneal shunts employed in pediatric neurosurgical techniques for release and fluid flow of cerebral-spinal fluids

BACKGROUND OF THE INVENTION

The present invention is usefully employed with ventricular catheters which have been therapeutically implanted in-vivo into the human brain; but which have become blocked by the surrounding cranial tissue which has occluded the intake drainage holes within the implanted catheter and become adherent to the catheter itself. In order to properly appreciate both the medical problem and the improved bipolar coagulator device which is employed therapeutically to alleviate such occlusion conditions in-situ, an in-depth description of the relevant medical and therapeutic use circumstances is provided below.

A. Ventricular Catheterization

The four ventricles of the human brain are interconnected cavities that produce and circulate cerebral-spinal fluid (CSF). Procedures involving ventriculostomy (i.e., placement of a catheter into the ventricular system of the brain) form a major part of a neurosurgeon's clinical practice. General areas for application of ventricular catheter placement include intracranial pressure monitoring (ICP), draining or shunting of CSF and the installation of pharmacological therapeutic agents.

CSF drainage is a major life-sustaining therapy for patients with congenital or acquired hydrocephalus. CSF drainage, which can only be performed with an intraventricular catheter, is a life-preserving procedure, because it can immediately reduce intracranial pressure. The ventricular catheter, used to drain cerebral-spinal fluid, is connected to a peripheral subcutaneous drainage system, i.e., to the peritoneal cavity or systemic circulation via the heart. However, later catheter obstruction by tissue and debris is a common, sometimes life-threatening problem.

Standard procedures for ventricular catheterization are disclosed in the textbook literature. See, for example, Neurosurgery, edited by Robert H. Wilkins and Setti S. Rangacharty, Section A, Chapter 13, Techniques of Ventricular Puncture (McGraw Hill 1984).

A frequently chosen site for ventricular catheterization is the coronal plane. In most cases, a catheter is inserted in the anterior horn of the lateral ventricle through an orifice or burr hole drilled just anterior to the coronal suture in the midpupillary line of the cranium, i.e., in the frontal bone over the ventricle. This is known in the field as Kocher's point. The burr hole, only slightly larger than the diameter of the selected catheter to insure a snug fit and provide a seal against CSF leakage, is placed approximately 1 cm. anterior to the coronal suture, approximately 10 to 12 cm. above the nasion, and approximately 2 to 3 cm. from the midline over the nondominant hemisphere. After the burr hole is made, the dura and underlying pia-arachnoid are opened and coagulated, for example, with a fine-tipped blade after cauterizing the dural surface.

A pre-measured catheter having a stylet is then introduced and directed freehand through the burr hole, approximately in the coronal plane, and angled towards the medial canthus of the ipsilateral eye, using external landmarks such as the inner canthus of the eye in the frontal plane and a point just in front of the external auditory meatus in the lateral plane as guides to placement. CSF should flow freely from the catheter tip at a depth of approximately 4 to 5 cm. from the interior cranial surface.

A distinctive "give", or release of opposition, can often be felt when the ventricle is penetrated. Pressure should be measured at this point, since an artificially low value will be obtained even if small amounts of fluid are lost. Then, after removal of the stylet from the catheter, advancement another 1 cm. or so should insure placement in the frontal horn at a depth of about 5 to 6 cm. from the external table of the skull, care being taken that CSF continues to flow.

A variety of ventricular catheters and a range of methods for guiding a catheter into the ventricular system of the human brain are conventionally known and used. Merely illustrating this range and variety are: U.S. Pat. Nos. 5,569,267; 5,030,223; 4,860,331; 4,613,324; 4,392,307; 4,386,602; 3,934,590; 3,223,087; 3,073,310; 3,053,256; 3,817,887; and the references cited within each of these printed publications.

B. Ventriculoperitoneal Shunts

Ventriculoperitoneal (VP) shunt placement for hydrocephalus is one of the most common procedures in neurological surgery. Hydrocephalus may result from subarachnoid hemorrhage, trauma, tumors, and the like. The technique entails introducing a catheter through brain tissue into one of the lateral ventricles of the brain. Cerebrospinal fluid in the ventricle may be vented through the catheter to relieve signs, symptoms, and sequelae of hydrocephalus.

The current surgical technique for placement of VP shunts was developed in the 1950s by Scarff and has persisted with few modifications. Despite the relative simplicity of this procedure, the complication rate can be significant and includes operative morbidity as well as post-operative infections and tissue obstructions.

Surgical technique plays a major role in reducing complications associated with VP shunts. Improper placement of the ventricular catheter may result in neurologic injury from the misplaced catheter or may cause an early proximal shunt obstruction, which is often secondary to blockage by adherent choroid plexus and other debris. The incidence of misplaced catheters is variable and dependent on a variety of factors, including the experience of the surgeon, the size of the targeted ventricle, the surgical approach, and the use of intraoperative guidance, such as fluoroscopy, ultrasound, or endoscopy. Thus, to optimize shunt function and minimize morbidity proper placement of the proximal catheter is essential.

Two surgical approaches have been principally used for VP shunt placement, frontal and parieto-occipital. To assist in placement into small ventricles, a frontal catheter guide has been developed by Ghajar for placement of frontal ventricular catheters [Ghajar J B, J. *Neurosurg.* 68: 318–319 (1988)]. This instrument capitalized on the anatomical observation that a line passing perpendicular to the skull at the coronal suture will intersect the lateral ventricle.

However, parieto-occipital catheter placement has some advantages over frontal catheter placement. The catheter path necessary for the frontal approach to the ventricles traverses frontal lobe regions having a low seizure threshold. Mechanical irritation of the neural tissue surrounding the catheter may give rise to epileptogenic foci independent of the underlying cause of hydrocephalus. This complicates patient management and increases health care cost, as well as markedly impacting the patient's quality of life.

The anatomy of the head and neck also cause technical difficulties for the surgeon. The distal end of the shunt is subcutaneously tunneled to the peritoneal cavity for implantation. Implantation in the open peritoneum provides an outlet for excess fluid drainage from the ventricles. The catheter path to the abdomen is circuitous from the frontal burr hole, however. The tube must pass posterior to the ear, and generally requires an additional skin incision. These difficulties frequently cause major complications and tissue obstructions.

C. Intraventricular Shunt Occlusions and Obstructions

Although generally successful and widely accepted by both neurosurgeons and patients, the ventriculoperitoneal shunt ("VPS") and indeed all shunting systems, regularly malfunction despite the best efforts of physicians and biomedical engineers. These malfunctions—once commonly the result of material, construction, or mechanical failures—now relate primarily to necessary compromises or technical errors occurring during shunt placement or revision that occur coincident to successful cerebrospinal fluid diversion. VPS malfunction rates are maximal during the first year after insertion (see Ventureya et al., Neurosurgery 34: 924–926 (1994)].

Malfunction is most commonly caused by obstruction of the ventricular catheter by choroid plexus, ventricular ependyma, or "debris". Ventricular catheter obstruction typically occurs in 80 to 90% of VPS malfunctions; and has become the predominant cause of obstruction because rigorous techniques have reduced the incidence of other causes of malfunction. Moreover, such ventricular catheter obstructions remain a major unsolved problem despite current improvements in materials or in catheter design changes, such as the Portnoy catheter [Haase et al., Acta Neurochir (Wien) 33: 213–218 (1976)]; and despite increased emphasis on precise techniques favoring optimal catheter placement [see for example: Ehni, G., Neurosurgery 14: 99–110 (1984); Epstein, F., Clin. Neurosurg. 32: 608–631 (1985); Gutierrez-Lara et al., J. Neurosurg. 42: 104–107 (1975); Nolsen, F. E. and D. P. Becker, Clin. Neurosurg. 14: 256–273 (1966) and J. Neurosurg. 20: 362–374 (1967)].

D. Prevention Of Intraventricular Shunt Occlusion And Obstructions

A ventricular tube, a catheter, having many sidewall holes in its head part and used for the above described purposes is well known, but these sidewall holes are often blocked by choroid plexus tissues which penetrate into the ventricular tube through the holes. In order to prevent this blockage, various device improvements have been proposed. These include the following illustrative examples: A drainage tube made of silicone [U.S. Pat. No. 4,182,343]; an external cerebrospinal fluid drain apparatus [U.S. Pat. No. 5,683, 357]; a drain cannula [U.S. Pat. No. 5,913,852]; and improved devices and methods for parieto-occipital placement of ventricular catheters [U.S. Pat. Nos. 5,569,267; 6,197,003; and 5,683,357].

In addition, a number of other innovations have been put forward as alternative preventative improvements. These are represented by an electrolyte fluid flow rate method and apparatus [U.S. Pat. No. 4,484,582]; an anti-siphoning valve [U.S. Pat. No. 5,634,894]; a method of screening for silicone-specific hypersensitivity [U.S. Pat. No. 5,747,270]; and a catheter advancing single-handed soft passer [U.S. Pat. No. 6,197,003].

E. In-vivo Treatments for Removing Occlusions and Obstructions from Ventricular Catheters Shunt malfunction usually demands elective, and often urgent, open surgical intervention to revise the shunt system and restore functional integrity before permanent brain injury occurs. Such revisions require general anesthesia in addition to the operative procedure and are followed typically by a minimum hospitalization of 2 to 3 days.

Once shunt function is restored, malfunction is most likely to recur in the next few weeks or months. Subsequent malfunctions and, necessarily, further surgical revisions are unfortunately not uncommon; and these carry significant risks of shunt infection, hemorrhage or bleeding difficulties, and seizures in addition to the emotional and chological trauma endured by patients and families [see for example: Ivan, L. P. and S. H. Choo, Can. J. Sure. 23: 566–568 (1980); Keuchner, T. R. and J. Mealey, J. Neurosurg. 50: 179–186 (1979); Shurin, S. and H. L. Rekate, J. Neurosurg. 54: 264–267 (1981)]. Revision of ventriculoperitoneal shunts is also the most common performed single neurosurigcal operation in the pediatric population. Pediatric ventriculoperitoneal shunts often occlude because the choroid plexus flows into the intake drainage holes in the ventricular catheter and then becomes adherent. This results in a proximal shunt malfunction requiring surgical revision. A significant complication of this revision surgery is that removal of the catheter can avulse the choroid plexus, causing intraventricular hemorrhage; and this can be dangerous by itself or cause a high risk of occlusion of the new shunt with debris or blood.

F. Monopolar Cauterization

Another frequent neurosurgical maneuver for removing shunt occlusions has been the use of a monopolar cautery. In typical usuage, a stilette is passed down the existing implanted catheter; and then the occluding tissue is coagulated with monopolar cautery to shrink the occlusion (typically the choroid plexus) and release the adhesion. This can be successful, but often can be complicated by concomitant damage to intracranial structures. Typically blood vessel damage and severe subarachnoid hemorrhages have been reported as a result of the monopolar coagulation technique. Nevertheless, monopolar cauterization continues to remain the conventionally accepted procedure and standard of care, despite the long-recognized dangerous and uncontrolled distribution of electric current and heat within the tissue which accompanies its use.

G. The Dangers and Disadvantages of Monopolar Cauterization

The medical dangers and substantive disadvantages of monopolar cauterization are perhaps best evidenced and exemplified by a brief, but revealing, patient case history—as reported by the authors, Drs. F. A. Boop and B. C. Cherny, at the 24th Annual Meeting of the American Society of Pediatric Neurosurgeons held Jan. 28-Feb. 2, 2001. Their published Abstract and patient case history is reproduced in full below.

"The authors present the case of an 8 year old child with congenital hydrocephalus, shunted in infancy, who presented with a proximal VP shunt malfunction. At the time of surgery, the ventricular catheter was stuck to the choroid plexus. The catheter was styletted and the choroid plexus coagulated with the monopolar bovic set on 30. The catheter was replaced uneventfully and the child sent home the next day doing well. He returned to the emergency room 2 weeks later with a spontaneous frontal lobe and intraventricular hemorrhage. At that time he was found to have a 1 cm pseudo-aneurysm arising from the anterior cerebral artery. In retrospect, the tip of the ventricular catheter extended to the level of the interhemispheric fissure. The authors believe that thermal injury from coagulation of the catheter caused the pseudo-aneurysm, which was subsequently treated endovascularly.

The authors suggest that, in cases in which ventricular catheter is in close proximity to major cerebral vessels, extreme caution be used in manipulating the catheter and that the current of the coagulating unit be turned down low prior to coagulating the anchoring tissues."

Accordingly, even though monopolar cauterization remains the current standard of care and therapeutic technique, it is clearly evident that an improved technology which is able to provide a better distribution of electric current and heat within the adherent tissue is both desirable and needed. Were a device to be developed which offers these desirable features and advantages and also allows for an easy utilization of the coagulation cauterization technique to remove adherent cranial tissue in-situ within a previously implanted ventricular shunt, such an innovation would be recognized and accepted by practitioners as offering major benefits and advantages as well as being a marked improvement in the relevant technical field.

SUMMARY OF THE INVENTION

The present invention provides a bipolar coagulator for in-vivo coagulation cauterization of tissue which is occluding at least one sidewall hole leading to the internal lumen of a catheter previously implanted into the body of a living subject for in-vivo flow release of fluids, said bipolar coagulator comprising:

a flexible obturator of fixed dimensions and substantially cylindrical form which is configured to fit within and pass through the inner diameter of the internal lumen of the catheter previously implanted in-vivo, said flexible obturator
  (i) comprising a shaped proximal end section adapted for passage within the inner diameter of the internal lumen of the implanted ventricular catheter, a distal end section, and a flexible body section adapted for passage through and around such internal lumen bends as may exist within the implanted catheter, and
  (ii) being constituted at least in part of an electrically insulating material;

at least two electrodes spatially disposed at different, direction-oriented, pre-chosen positions on said exterior surface of said proximal end section of said flexible obturator, each of said electrodes comprising a discrete electrode tip disposed on said exterior proximal end surface of said obturator at a pre-chosen position and an electrically communicating electrode body which is joined to said electrode tip and which extends into the interior of said obturator, said at least two direction-oriented disposed electrodes providing at least one positively charged electrode pole and at least one negatively charged electrode pole which collectively identify (a) a demarcated surface area between said disposed electrode poles on said exterior surface of said obturator,
(b) a discrete gapped space which exists adjacent to and over said demarcated surface area between said disposed electrode poles as a cauterization zone, and
(c) an on-demand electrode system for generating a direction-oriented and spatially-controlled flow of electrical arc current for coagulation cauterization over said gapped space of said obturator; and
electrical current conveyance apparatus which is contained internally at least within said proximal end section of said obturator and is joined to each electrode spatially disposed on said surface of said obturator.

BRIEF DESCRIPTION OF THE FIGURES

The present invention may be more easily understood and more readily appreciated when taken in conjunction with the accompanying drawing, in which:

FIG. 1A illustrates a conventionally known ventricular catheter while FIG. 1B shows a perspective view of a dimensionally sized bipolar coagulator able to pass through the ventricular catheter in-situ;

DETAILED DESCRIPTION OF THE INVENTION

Figures 1A, 1B:
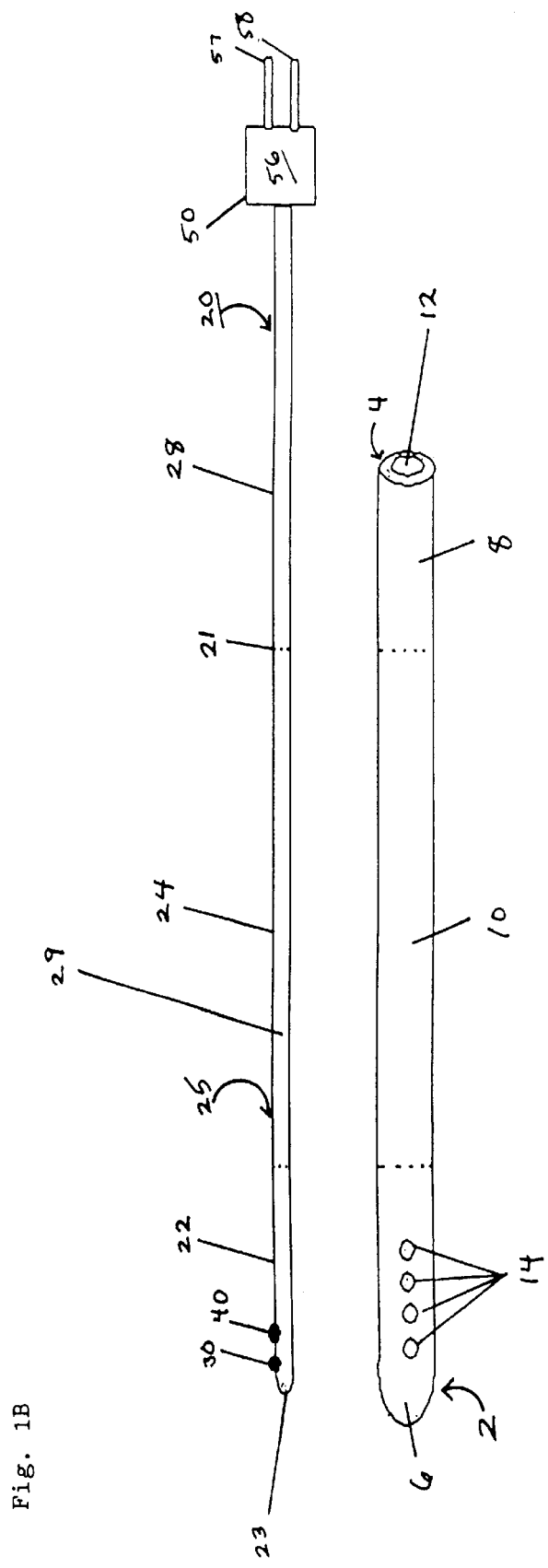

The present invention is a bipolar coagulator for in-vivo coagulation of cranial tissue which is occluding at least one sidewall hole in the internal lumen of a ventricular catheter previously implanted into a cranial ventricle of a living subject for in-vivo flow release of cranial fluids such as cerebral-spinal fluid. The bipolar coagulator comprising the present invention may be fashioned in the alternative using different materials; may be formed into a variety of different shapes and dimensions to meet the individual purpose or use circumstance; and may employ one or more sets of electrodes which provide direction-oriented and spatially-controlled coagulation and cauterization current in-situ for the removal of adherent cranial tissues (such as the choroid plexus) which then occlude the intake drainage holes in the implanted ventricular catheter in-vivo. A detailed description of the different embodiments envisioned and intended for the bipolar coagulator is given below.

I. Embodiments of the Bipolar Coagulator

The essential description of the bipolar coagulator with reference to a previously implanted ventricular catheter is shown by FIGS. 1A, 1B, 2 and 3 respectively. As appears in FIG. 1A, a conventional ventricular catheter 2 is shown in detail. The ventricular catheter 2 is an elongated tube having a circular sidewall 4, a proximal end 6, an elongated body 10 of predetermined axial length, and a distal end 8. The ventricular catheter 2 also comprises an internal lumen 12 of fixed inner diameter which extends from the distal end 8 to the proximal end 6. In addition, at the proximal end 6 are multiple sidewall holes or ports 14 which lead into the internal lumen 12 of the ventricular catheter 2 and allow for the flow release of fluids.

The ventricular catheter illustrated by FIG. 1A is exemplary and representative of the conventionally known range and variety of catheters employed for this purpose generally; and is illustrative of the catheters commonly employed as ventriculoperitoneal (VP) shunts in neurological surgery for release of fluids from the cranium.

An exemplary bipolar coagulator device comprising the present invention is shown in relative dimensional relationship by FIG. 1B with respect to the size and shape of the ventricular catheter shown by FIG. 1A. Accordingly, the bipolar coagulator 20 is shown in perspective view by FIG. 1B and is revealed in an enlarged, cross-sectional view by FIG. 2.

The bipolar coagulator 20 comprises a flexible obturator 21 of fixed dimensions and substantially cylindrical form which is configured to fit within and pass through the inner diameter of the internal lumen 12 of the ventricular catheter 2. It is presumed, of course, that the ventricular catheter 2 has been previously implanted in-vivo and that it has become occluded by cranial tissue in-situ.

The flexible obturator 21 comprises a shaped proximal end section 22 of determinable axial length and is adapted for passage within the inner diameter of the internal lumen 12 of the implanted ventricular catheter 2; a distal end section 28 of determinable axial length; and a flexible elongated body section 24 of determinable axial length and which is adapted for passage through and around such internal lumen bends as may exist within the implanted ventricular catheter in-situ.

The flexible obturator 21, as a requisite component part of each bipolar coagulator embodiment, typically presents a contiguous exterior surface 25 which is compatible with the exposed surface forming the internal lumen of in the ventricular catheter 2 implanted in-vivo; and is constituted at least in part of an electrically insulating material 27 over the axial length of the obturator 21 as a whole.

Figure 2:
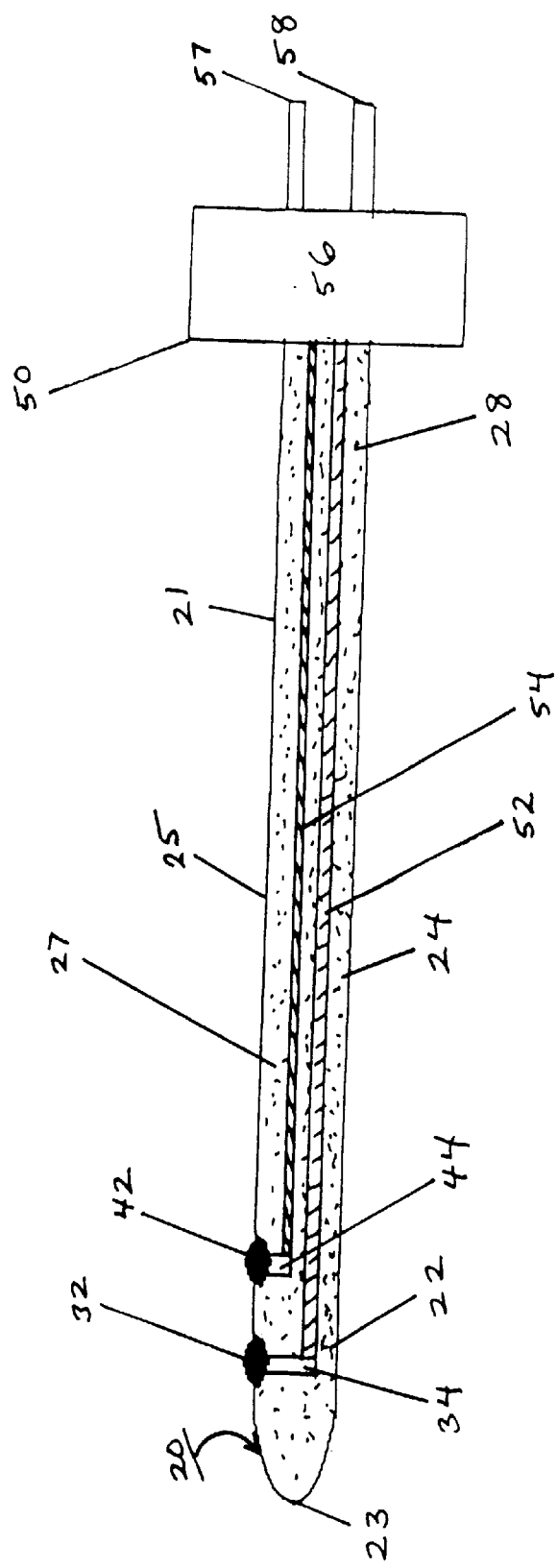
FIG. 2 is a cross-sectional view of the bipolar coagulator shown by FIG. 1B.
Figure 3:
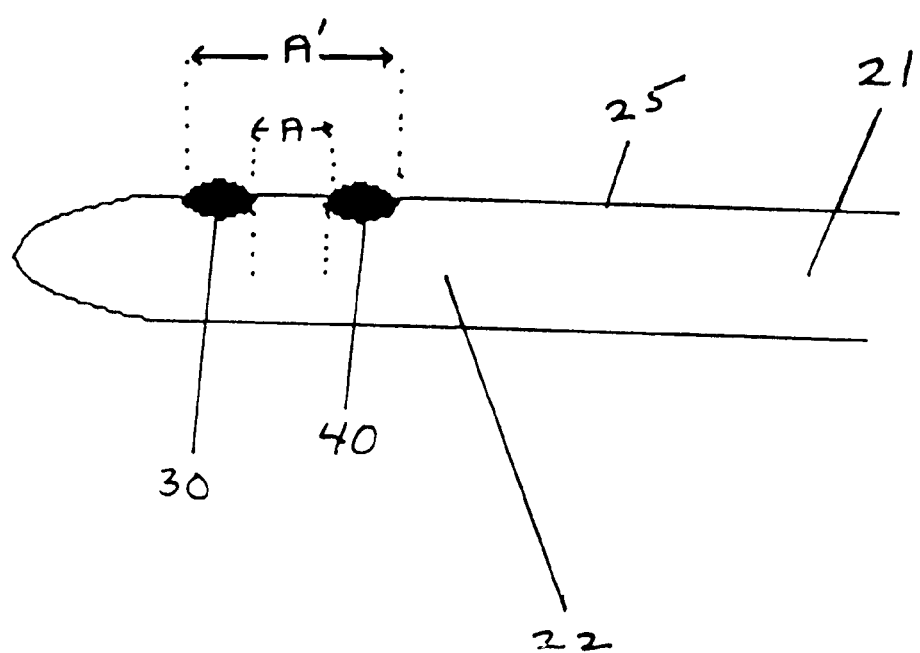
FIG. 3 is a perspective view of the proximal end of the bipolar coagulator shown by FIG. 1B.

As shown by FIGS. 2 and 3 respectively, there are at least two electrodes 30, 40 spatially disposed at different, direction-oriented, pre-chosen positions on the exterior surface 25 of the proximal end section 22 of the flexible obturator 21. Each of these at least two electrodes 30, 40 respectively individually comprises a discrete electrode tip 32, 42 disposed on the exterior proximal end surface of the obturator 21 at an individual pre-chosen position; and an electrically communicating electrode body 34, 44 which is joined to each said electrode tip 32, 42 and which extends into the interior 29 of the obturator. Moreover, the at least two direction-oriented disposed electrodes provide for the presence of at least one positively charged electrode pole 30 and at least one negatively charged electrode pole 40.

In addition, these direction-oriented disposed electrodes 30, 40 collectively identify the following features, as shown in FIG. 3: A demarcated and fixed surface area A lies between the individually disposed electrode poles 30, 40 on the exterior surface 25 of the obturator 21 and serves as a discrete operative sector. Also, a discrete gapped space A' exists adjacent to and immediately over the demarcated surface area A (lying between the individually disposed electrode poles 30, 40) and serves as a marked-out cauterization zone. Finally, an on-demand electrode system exists for generating a direction-oriented and spatially-controlled flow of electrical arc current for coagulation cauterization over the cauterization zone lying adjacent to and directly over the demarcated surface area of the obturator.

The bipolar coagulator article as a whole also comprises an electrical current conveyance apparatus 50 which is seen in FIGS. 1B and 2 respectively. The electrical current conveyance apparatus 50 is contained internally at least within the proximal end section 22 and the elongated body section 24 of the obturator 21; and is joined to each electrode 30, 40 individually—each of which is spatially disposed on the exterior surface 25 of the obturator 21.

The electrical current conveyance apparatus includes at least two electrode cables 52, 54; a conveyance connecting housing 56; and current connector tips 57, 58 which extend from the connecting housing 56 lying at the distal end section 28 of the obturator 21. The electrical current conveyance apparatus 50 is the tangible means and mechanism by which electrical current from an outside source is delivered internally within the obturator 21 to each of the electrodes 30, 40 respectively which are spatially disposed on the exterior surface 25 of the obturator 21. In this manner and by the deliverance of charged electrical current via the electrode cables 52, 54, an electrically charged positive pole 30 and an electrically charged negative pole 40 is generated on-demand.

Figure 4:
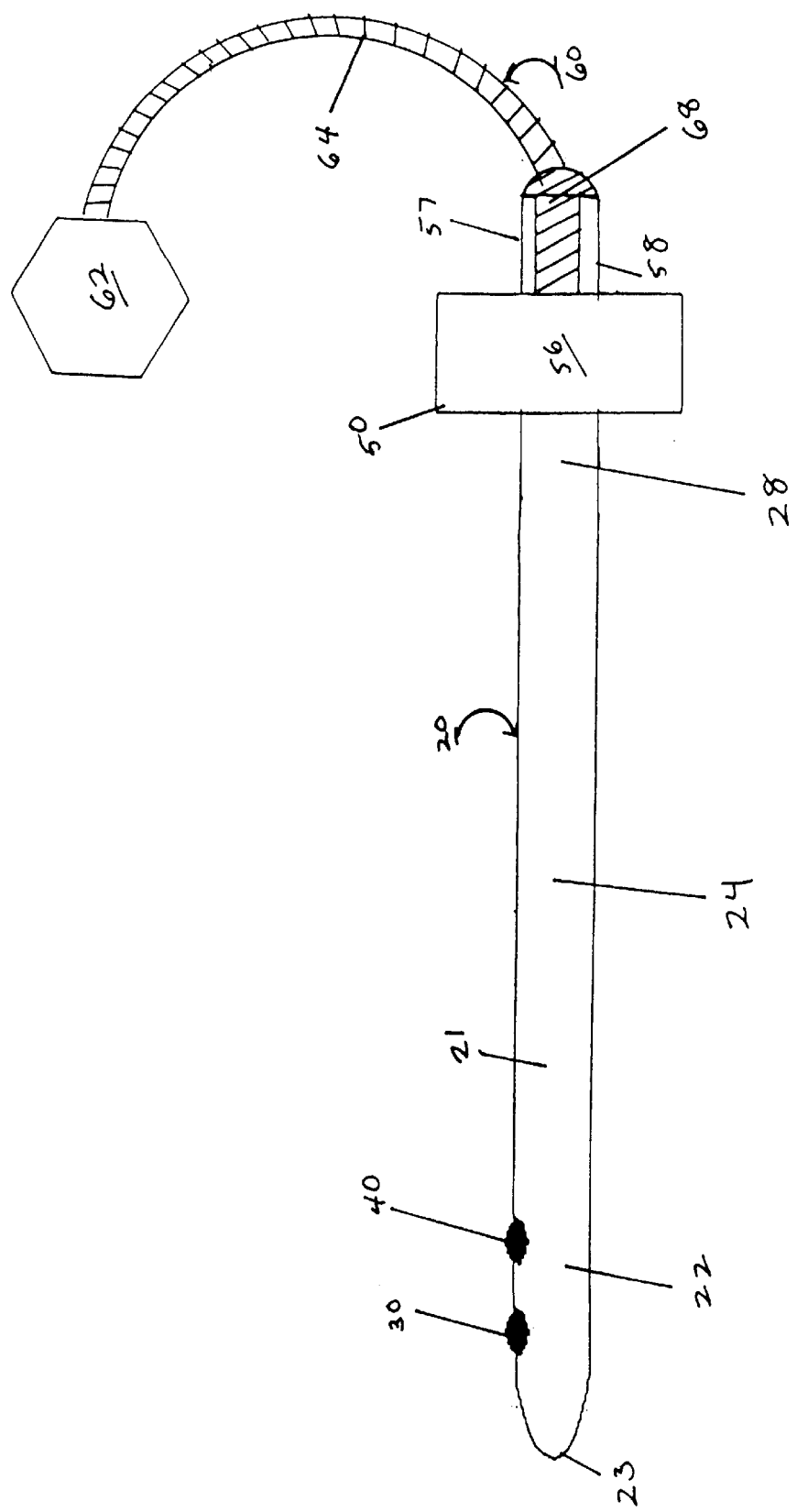
FIG. 4 is a perspective view of the complete bipolar coagulator shown by FIG. 1B.

The complete bipolar coagulator assembly is shown by FIG. 4. As seen therein, the bipolar coagulator 20 is joined to and is in electrical current flow communication with an external source of electrical power 60 comprising a power source 62, a connecting line 64, and a receptacle adaptor 66 which is configured for direct contact with an electrical juncture to the current connecting tips 57, 58 of the electrical current conveyance apparatus 50. The external source of electric power 60 is conventionally known; can be located remote from or lie in direct intimacy with the bipolar coagulator itself; can be battery-operative; or can alternatively be a generator able to supply sufficient quantities of electrical current at will—i.e., whenever required by the surgeon or medical practitioner utilizing the bipolar coagulator unit for its intended purpose.

A First Alternative Embodiment

Figure 5:
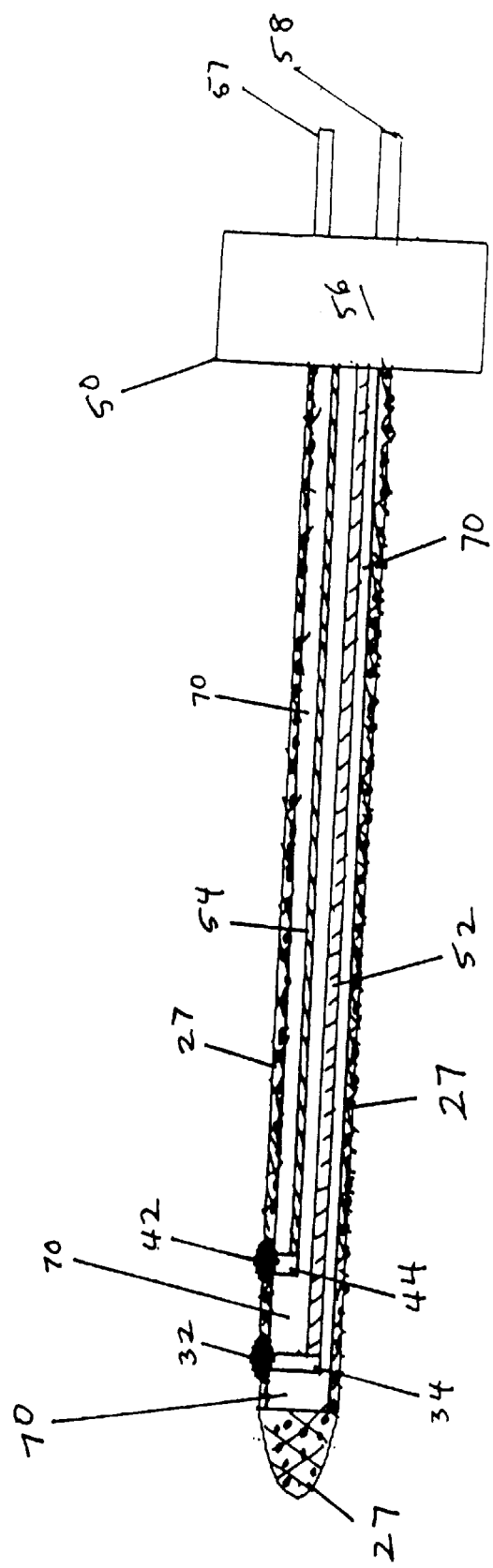
FIG. 5 is a cross-sectional view of a first alternative embodiment for the bipolar coagulator.

A first alternative embodiment and variation from the minimal structure illustrated by FIGS. 1B, and 2–4 respectively is shown by FIG. 5. A single, but often desirable, structural feature appearing in this first alternative embodiment is shown as an obturator 21 which now further comprises at least one internal body cavity 70. As shown, this internal body cavity 70 preferably extends from the proximal end section 22, through the elongated body section 24, into the distal end section 28; and terminates at the location where the electric current conveyance apparatus 50 is physically joined to the distal end section 28 of the obturator 21. The internal body cavity 70 shown within FIG. 5 appears a single hollow space; but alternatively can be fashioned as multiple hollow air cavities with intervening solid walls appearing wherever and however desired within the elongated body section 24 and distal end section 28 of the obturator 21. Also, in the embodiment shown in FIG. 5, the cables 52, 54 of the electric current conveyance apparatus 50 lie positioned within the hollow cavity 70 over the entirety of their axial lengths; and are joined to the electrode bodies 34, 44 of the electrodes 30, 40 respectively within the air space encompassed by the hollow cavity 70.

It will be noted and appreciated also, however, that the first alternative embodiment illustrated by FIG. 5 reveals that the obturator 21 is comprised of electrically insulating material 27, which both internally surrounds the hollow cavity space 70 as well as provides a solid contiguous exterior surface 25 upon which the electrode tips 32, 42 are spatially disposed. This first alternative embodiment is identical to that shown previously by FIG. 2 in all other respects.

A Second Alternative Embodiment

Figure 6:
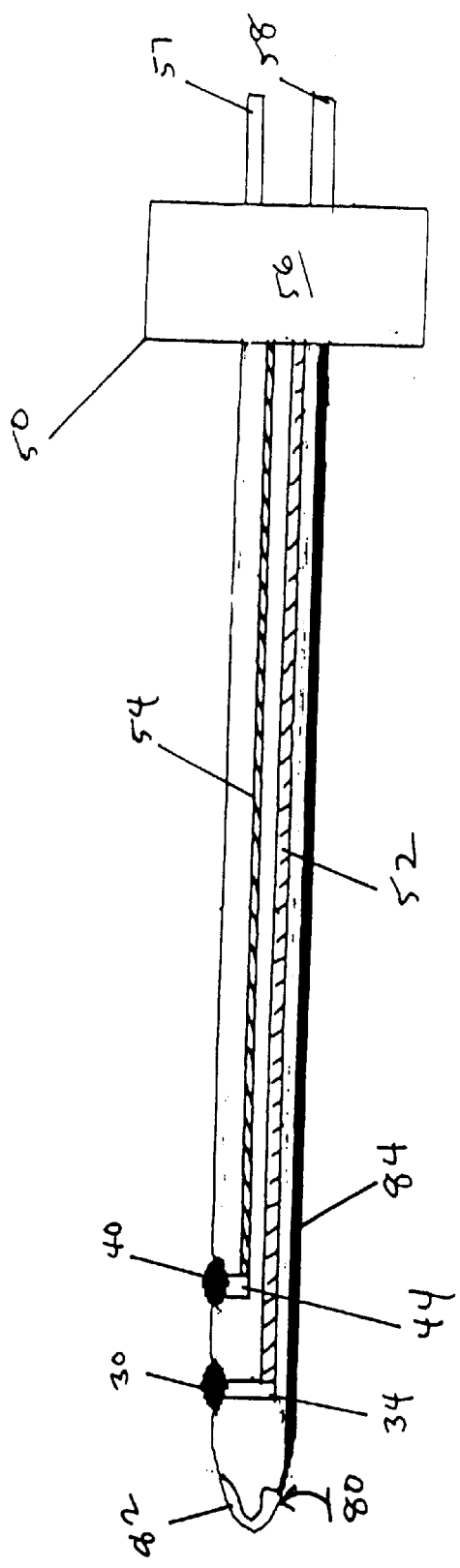
FIG. 6 is a cross-sectional view of a second alternative embodiment for the bipolar coagulator.

A second alternative embodiment provides a desirable variation from the minimal features shown by FIGS. 2–4 respectively; and is illustrated by the bipolar coagulator structure shown by FIG. 6. As seen therein, a new feature and component part of the bipolar coagulator 20 appears in cross-sectional view as a sensory apparatus 80 which comprises a sensor array 82 and a connecting lead 84. The sensor apparatus 80 utilizes the sensor array 82 disposed at the apex 23 at the proximal end section 22 of the obturator 21; and the connecting lead 84 extends internally within the interior of the obturator from the sensor array 82 over the axial length of the obturator body to the electrical current conveyance apparatus 50 and the conveyance connecting housing 56 in particular, from which the sensing data can be accessed.

One format of this sensor apparatus is as an electrical impedance measuring device, by which the electrical impedance is measured when the adherent tissue occluding the sidewall holes in the ventricular catheter is encountered. The observed and measured impedance values will be an indicator that the occlusion site has been reached within the internal lumen of the implanted catheter.

In addition, the sensor apparatus may also be formatted as and comprise a small thermal coupling or other temperature measuring article incorporated into the sensor apparatus as a whole. Such temperature monitoring sensor would then measure the temperature and heat distribution both during and after the application of electrical cauterization current to the adherent tissues internally. Such temperature monitoring will ensure that excessive heat is not generated during the typical usage of the bipolar coagulation device. In all other respects, features, and structures, this second alternative embodiment of FIG. 6 is substantially identical to that device previously described herein.

A Third Alternative Embodiment

Figure 7B:
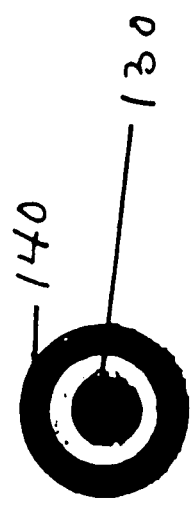
FIGS. 7A and 7B are a side view and a frontal view of a third alternative embodiment for the bipolar coagulator.
Figure 7A:
Figure 8:
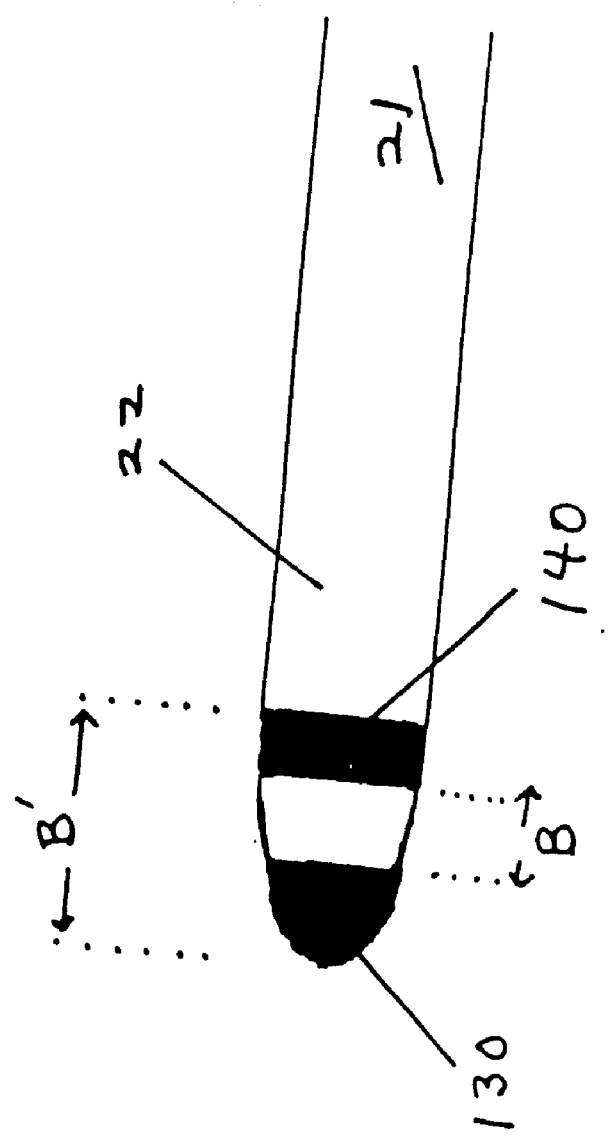
FIG. 8 is a detailed side view of the third alternative embodiment shown by FIGS. 7A and 7B.

A desirable third alternative embodiment of the bipolar coagulator assembly and device is illustrated by FIGS. 7A, 7B, and 8 respectively. In this third alternative embodiment, an alternative disposition of two electrodes at different direction-oriented pre-chosen positions on the exterior surface is shown. In particular, two electrodes 130, 140 respectively are spatially disposed at unique locations and pre-chosen positions on the exterior surface 25—that is, at the apex 23 and the area surrounding the apex at the proximal end section 22 of the flexible obturator 21. Each of these two electrodes 130, 140 comprises a discrete electrode tip disposed on the exterior proximal end surface of the obturator at an individual pre-chosen position and an electrically communicating electrode body (not shown) which is joined to the electrode tip and which extends internally into the interior of the obturator.

The two apex-disposed electrodes 130, 140 respectively provide at least one positively charged electrode pole and at least one negatively charged electrode pole, which collectively identify: a demarcated and fixed surface area B lying between the individually disposed electrode poles 130, 140 on the exterior surface 25 of the obturator 21 and which serves as an operative sector; a discrete gapped space B' which exists adjacent to and immediately over the demarcated surface area B located between the individually disposed electrode poles 130, 140 and which serves as a marked-out cauterization zone; and an on-demand electrode system for generating a direction-oriented and spatially-controlled flow of electrical arc current for coagulation cauterization over the gapped space lying adjacent to and immediately over the demarcated surface area of the obturator.

In appearance, a "bulls-eye" effect is created by the two electrodes 130, 140 positioned at and around the apex 23 on the proximal end sector exterior surface. It will be noted and appreciated that the positively charged electrode 130 is disposed at the apex 23 itself, while the negatively charged electrode pole 140 lies at a fixed spatial distance from the positive pole on the exterior surface and encompasses the apex proper. The demarcated surface area B lying between the positively charged electrode 130 and the negatively charged electrode 140 may vary in fixed distance considerably; and the demarcated surface area B also may be narrow or broad, so long as it exists as an operative sector over which a flow of electrical arc current will pass on-demand from the positive pole to the negative pole in the amperage and voltage required.

As seen in the frontal view provided by FIG. 7B, the "bulls-eye" appearance is clearly visible; and the flow of direction-oriented and spatially-controlled electric arc current will transverse the gapped space B', which exists adjacent to and immediately over the demarcated surface distance B lying between the individually disposed electrode poles. This gapped space B' determines and provides a clearly marked cauterization zone over which the electric arc current will flow on-demand. In this manner, an electrode system capable of generating a direction-oriented and spatially-controlled flow of electrical arc current for coagulation purposes exists which is effective over both the gapped space and the demarcated surface area lying between the disposed electrode poles on the exterior surface of the obturator.

It is understood also that each electrode 130, 140 individually includes and comprises an electrical current conveyance apparatus comprising individual electrode cables, a conveyance connector housing, and current connector tips similar to if not identical to that shown in previous embodiments herein. The other structural requirements and features described earlier herein are included for this alternative embodiment as well.

A Fourth Alternative Embodiment

Figure 9:
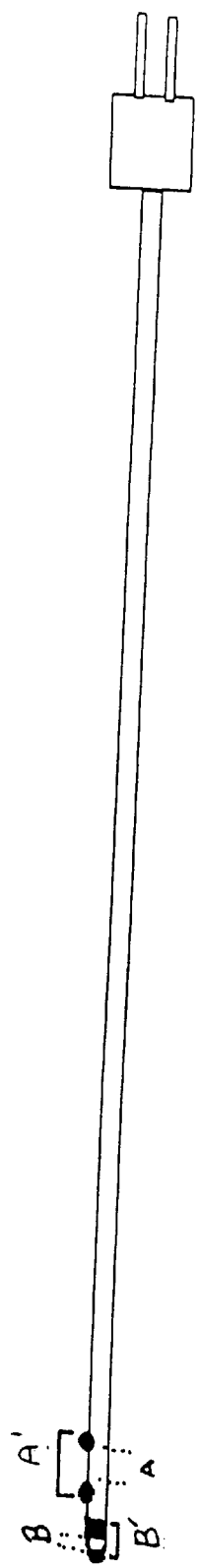
FIG. 9 is a perspective view of a fourth alternative embodiment for the bipolar coagulator.

A desirable fourth alternative embodiment is illustrated by FIG. 9, which is in fact a combination of the embodiments previously described herein and illustrated by FIGS. 3 and 7. As seen in FIG. 9, two sets of electrode pairs are spatially disposed at different, direction-oriented, pre-chosen positions on the exterior surface of the proximal end section of the flexible obturator. Please note that each paired set of electrodes 30, 40 and 130, 140 respectively comprises a discrete electrode tip disposed on the exterior proximal end surface of the obturator; is disposed at individual pre-chosen positions; and includes an electrically communicating electrode body which is joined to each electrode tip individually and which individually extends into the interior of the obturator.

Note also that each paired set also provides at least two direction-oriented disposed electrodes in which each pair includes at least one positively charged electrode pole and at least one negatively charged electrode pole. Each pair of electrically charged electrodes thus collectively identifies an individual demarcated surface area and distance A lying between the individually disposed electrodes poles on the exterior surface. Consequentially, the demarcated surface area A for the electrodes 30, 40 is in existence, while the other demarcated surface area B concurrently exists between the individually disposed electrode poles 130, 140. In similar fashion, each pair of electrode poles provides a discrete gapped space A' and B' respectively, each of which exists adjacent to and immediately over each demarcated surface area A and B respectively, lying between the individually sets of electrode poles. Thus each paired set of electrodes has an individual cauterization zone, A' or B' respectively.

Finally, the two paired sets of electrodes also provide an on-demand electrode system in which each pair of electrodes generates an individual and different direction-oriented and spatially-controlled flow of electrical arc current for coagulation purposes on-demand. Thus, for the electrode pair 30, 40, an electric arc will be generated over and through the gapped space A'; while electrode pair 130, 140 offers a spatially-controlled flow of electric arc current over the gapped space B' which is itself direction oriented. In this manner, two different electrical arc currents may be employed either individually, or alternatively, or concurrently, or simultaneously for on-demand coagulation of occluding tissue in-situ.

The pair of charged electrodes 130, 140 generates on-demand an electrical arc current around the apex while the electrode pair 30, 40 generates an electrical arc current on-demand along the sidewall along the proximal end section of the obturator. In this manner, electrical cautery current can be generated at will, at different locations, when and as needed to meet individual use circumstances.

A Fifth Alternative Embodiment

Figure 10:
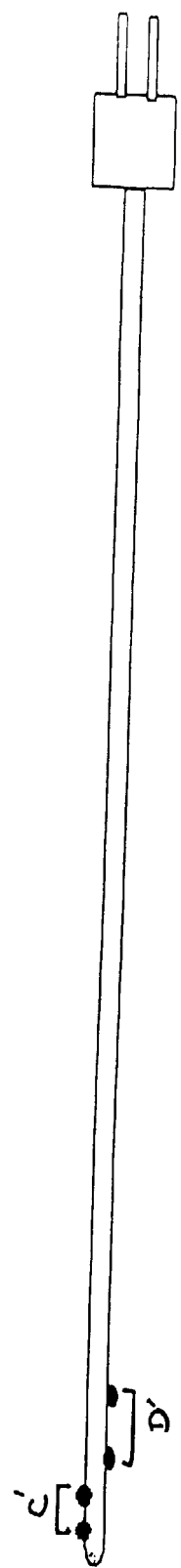
FIG. 10 is a perspective view of a fifth alternative embodiment for the bipolar coagulator.

Another disposition of two different sets of electrodes is shown by FIG. 10 in which two sets of electrodes are positioned on the surface of the obturator, but on different sides of the proximal end section surface. As appears in FIG. 10, a discrete gapped space C' exists adjacent to and immediately over the demarcated sidewall area near the apex, while a second discrete gapped space D' concurrently exists as a marked-out cauterization zone on the other side of the proximal end section. Each set of electrodes provides a different and individual discrete gapped space for the generation of electrical arc current on-demand.

It will be recognized and appreciated also that many other positional dispositions of electrode pairs and of positive and negatively charged electrode poles can be made as desired at different pre-chosen positions on the proximal end section surface of the obturator—wherever and however desired or deemed to be of utilitarian service. It is expected that multiple pairs and sets of electrodes will be disposed at many different locations on the exterior surface of the flexible obturator; and that each disposed set will comprise at least two electrodes which are direction-oriented and spatially-controlled, thereby providing a on-demand generation of electrical arc current for coagulation cauterization over a discrete spatial gap (which exists adjacent to and over the demarcated surface area lying between each set of individually disposed electrode poles).

II. Pertinent Features and Parameters

A. Obturator Structure Design

Several specific structural features are necessary in order to have a bipolar coagulator which is functional for coagulation cauterization of cranial tissue or other kinds of tissue which then occlude at least one sidewall hole leading to the internal lumen within a catheter previously implanted in-vivo. These include the following:

1. The length of the obturator and the bipolar coagulator as a unit should be long enough to reach the tip of the shunt catheter from the burr hole. Ventricular catheters typically range from about 3 cm. to about 12 cm. in length. The axial length of the obturator must therefore be greater than 12 cm., and often is as much as 15 cm. in length.

2. The diameter of the obturator must be able to fit within and pass through the typical range of inner diameters for ventricular catheters conventionally used and currently in place. A typical inner diameter for ventricular catheters thus is 1.3 mm ID (Integra Neuro Sciences, Pudenz Ventricular Catheter). The thickness and girth of the obturator should also be able to pass some debris that may be present on the surface of the inner sidewalls in the internal lumen of the ventricular catheter. Therefore, a reasonably useful obturator diameter is about 1 mm in size. Equally important, the overall diameter of the obturator must be large enough to prevent it from passing through any sidewall holes in the ventricular catheter; and the 1.0 mm diameter size would suffice for this as well.

3. The material of construction for the obturator is merely a question of particular preference or personal convenience. The exterior surface of the obturator, which may exist and be constructed as a distinct covering or structural layer of matter, is desirably formed of an electrically insulating material; and the overall flexibility and stiffness of the obturator as a structural entity is chosen such that it would easily return to a substantially straight, linear orientation and position, but also would be able to be easily deflected, bent, or become curved in order to accommodate the internal lumens of catheters that have become demonstrably bent as a consequence of implantation. The recognized flexibility of Silastic polymer is deemed to be both acceptable and desirable for this purpose.

4. The pre-positioning of electrodes and electrode tips on the exterior proximal end surface of the obturator is both critical and essential. The charged positive and negative poles of the bipolar coagulator must be able to reach and lie adjacent to the sidewall holes leading to the internal lumen of the catheter. Such sidewall holes are typically within 1 to 2 cm. distant from the implanted tip end of the ventricular shunt tubing. In most instances, therefore, it will be necessary to situate at least the minimal two electrode tips close to or directly at the apex of the shaped proximal end section of the obturator.

5. The spatial orientation and directional design of the disposed electrodes and electrode tips is also important. A central feature and advantage of the present bipolar coagulator is that at least two charged electrode tips are available for bipolar coagulation cautery currents. These positively and negatively charged electrodes can be mounted on the exterior surface of the obturator at the very apex of the obturator with a "target" configuration (effectively creating an operational "bull's-eye" appearance) which is oriented and aligned spatially to cauterize the exposed surface of the internal lumen at the implanted end tip of the ventricular catheter. Such surrounding, concentric circles of surface disposed electrodes will provide for bipolar cauterization of occluding cranial tissue that would be found directly and immediately in front of the obturator.

An alternative electrode positioning would place the two charged electrode poles of the bipolar coagulator on the sidewall, rather than at the apex, of the obturator, for controlled side coagulation cauterization. As before, this manner of electrode disposition and pre-chosen positioning would have a radial symmetry—with the surface disposed electrodes completely encircling the obturator, and being electrically joined by current conveyance cables which would pass internally down the stem of the obturator, to an outside source of electrical energy (such as an electrical generator).

Alternatively again, each of the minimal two electrode poles could encompass and circumscribe less than half of the obturator circumference and perimeter; and these pre-positioned spatially oriented electrodes could be disposed side-by-side in juxtaposition if desired, which would allow radial or axial directionality in the technique of coagulating.

6. The electrodes and electrode tips of the bipolar coagulator are preferably attached electrically and are in electrical current flow communication with an external pulse generator, a conventionally known and commercially available device which is used for other forms of bipolar cauterization currently. A "tail" of the wire could extend from the electrical conveyance connector end of the obturator for ease of use, or the electrode cables extending from the pulse generator could be connected directly through the axial length and substance of the obturator to the pre-positioned electrodes disposed on the obturator surface.

B. Preferable Control Parameters and Features

Several parameters are under control of the surgeon to achieve the correct amount of coagulation. The first involves the passage of the obturator down the ventricular catheter shunt tubing. The stiffness characteristics of the bipolar coagulation device make it possible to palpate the possibly obstructing tissue en route in and coagulate whenever an obstruction is met. A firm end obstruction would be felt when the tip of the catheter is reached, so that the bipolar obturator does not get passed out of the shunt into the brain.

Second, the electrical settings and standard of switch activator of the bipolar cautery (with foot-plate activation or other) controls the actual amount of current and current distribution within the brain.

Third, the electrical impedance measurements of this bipolar coagulation device show the impedance value to be substantially equivalent to the conventionally known and popularly used bipolar electrocautery forceps at the appropriate frequency. Accordingly, the energy distribution within living tissue is predictable, and has been seen and observed by the surgeon at any given electrical setting.

C. Other Desirable Features

While the above description presents the necessities of this bipolar coagulator structure, several additional features are desirable in the realization of personal choices.
Temperature Monitoring:
A small thermal couple or other temperature measuring device can be placed and incorporated into the proximal end section and/or apex of the obturator to monitor the cauterization effect (temperature and heat distribution) on local cranial tissues and to be sure that excessive heat is not generated during typical usage of the bipolar coagulator device. Similarly, such a monitoring sensor array could inform the user if adequate coagulation had occurred in-situ at the implanted end of the ventricular catheter.
Impedance Monitoring:
By measuring the electrical impedance across the electrodes as the obturator is passed down the internal lumen of the implanted ventricular catheter, the change of impedance values caused via the replacement of cerebrospinal fluid by solid (occluding) tissue would indicate to the surgeon that abnormal obstructions have been encountered, and perhaps should be coagulated (to remove them). This is a direct sensory determination and an important measurable value feedback of information for the surgeon.
Irrigation:
Irrigation of debris out a central hole in the ventricular catheter tubing or as a fluid flow along the external surface and sides of the obturator would help remove debris and also could be used with the interfaces conventionally available for typical irrigation of bipolar coagulators with prepared sterile irrigation fluid.
Pressure Wave form Determination:
Since restitution of an adequate cranial fluid release and cerebrospinal fluid flow within the ventricle catheter might occur with an increase in the pulsatile pressure profile, a simple pressure transducer can be included in the end tip or at a more proximal site on the sidewall of the catheter with output measured electronically and conducted to a pressure display available to the surgeon.

III. Mode of Operation

This bipolar coagulator device is structured for insertion into the ventricular end of a ventricular CSF shunt when an occlusion or an obstruction is suspected. Typically, during a shunt revision, either open or percutaneous, the obturator of the bipolar coagulator would be passed directly down the open end of the previously implanted ventricular catheter or inserted and passed through a small pinhole in the reservoir over the ventricular catheter which is made by the operating surgeon for this purpose. When small amounts of resistance are encountered to palpation, occluding tissue in the lumina is suggested and bipolar coagulation cautery current may be applied.

Other sensors and parameters indicative of obstructing cranial tissue, such as electrical impedance value changes, may also be used as described above. At any point of presumed occlusion or obstruction, the cauterizing current generated by the bipolar coagulator may be turned on at will; and the obturator may then either be rotated or slowly axially advanced as needed for continued coagulation of all of the occluding or obstructing intraluminal tissue debris. Assessment of the completeness of occluding tissue removal can be done either by removing the obturator and seeing if CSF flow is restored; or detecting a release and flow of CSF fluid using one or more of the desirable additional features, such as pressure-measuring sensors, included as part of the obturator structure.

Alternatively, if a surgical removal and complete replacement of the existing ventricular catheter is desired or considered medically prudent, experience has shown that coagulating the adherent cranial tissue can often allow the catheter to be pulled out with little risk of bleeding; but if the catheter to be surgically excised is pulled back slightly and there is still significant resistance, then the entire bipolar coagulation procedure can be repeated as needed in order to coagulate more of the obstructing tissue in-situ. Moreover, if the catheter to be surgically excised is pulled back until there is a small amount of tension on it, passing the obturator down to the point of obstruction and again coagulating the adherent tissue in-situ may cause the catheter to suddenly become released; and the catheter can be withdrawn then in-toto with greater safety to the patient.

IV. Method for Using the Bipolar Coagulator Device (a) Introduction of the bipolar coagulator into the ventricular catheter requires inserting the bipolar coagulator device either through a skin opening (as in traditional shunt revision surgery, done in an operating room under sterile conditions); or using a percutaneous technique wherein a needle large enough to accommodate the coagulator is introduced through the appropriately prepared skin into the shunt (typically through a self-sealing membrane), so that the coagulator can be advanced into the ventricular end of the shunt system.

(b) Depth of penetration of the device into the shunt system, the implanted catheter, is assessed by the operating surgeon according to the sensory feedback of the device, which indicates when the terminus of the catheter is reached; or is determined when resistance to advancement suggests to the surgeon that obstruction of the catheter due to tissue or debris is encountered before reaching the expected end of the catheter, based on information about its length (such as from radiographic images or surgical notations).

(c) Once obstructions are encountered or the end of the catheter is encountered, electrical activation of the device with bipolar coagulating currents can then be used to coagulate or fulgurate the tissue obstructing the catheter.

(d) Manipulation of the coagulator device (such as rotation to change the directional orientation), or substitution of the device for another which is more suitable for the particular geometric configuration of the implanted catheter, may be needed to optimize coagulation of the obstructing tissue.

(e) The completion of adequate coagulation can be determined from clinical criteria used currently with the (less satisfactory) monopolar coagulation. These criteria include: increasing CSF flow around the coagulator, or release of resistance to withdrawal of the catheter. If more specific feedback systems are included in the particular embodiment of the device, then other criteria may also be used to determine when coagulation is complete. These alternatives thus may include: improvement in the pulsatile flow by direct pressure measurements; changes in electrical impedence; or attainment of a particular limiting temperature in the surrounding tissue.

(f) After coagulation is completed by one or all of the above criteria, the bipolar coagulator device is removed. The operating surgeon has the option to replace the catheter or to leave it in place, if the implanted catheter is then thought to be functioning adequately.

(g) After assuring that the catheter shunt is working adequately, all other apparatus is then removed; and, if an open surgical operation was performed, the surgical incision is properly closed.

The present invention is not to be restricted in form nor limited in scope except by the claims appended hereto.

What I claim is:

1. A bipolar coagulator suitable for passage through the internal lumen of a catheter and for in-vivo coagulation cauterization of tissue then occluding at least one sidewall hole leading to the internal lumen of a catheter previously implanted into the body of a living subject for in-vivo flow release of fluids, said bipolar coagulator comprising:
    a sized flexible obturator of fixed dimensions and substantially cylindrical form which will fit within and pass through the inner diameter of the internal lumen of the catheter previously implanted in-vivo, said sized flexible obturator
        (i) having a shaped proximal end section able to pass within the inner diameter of the internal lumen of the implanted catheter, a distal end section, and a flexible body section able to pass through and around such internal lumen bends as exist within the implanted catheter, and
        (ii) being constituted at least in part of an electrically insulating material;
    at least two electrodes spatially disposed at different and direction-oriented positions on the exterior surface of said proximal end section of said flexible obturator, wherein each of said electrodes comprises a discrete electrode tip disposed on said exterior proximal end surface of said obturator at a pre-chosen position and an electrically communicating electrode body which is joined to said electrode tip and which extends into the interior of said obturator, and whereby said at least two direction-oriented disposed electrodes present at least one positively charged electrode pole and at least one negatively charged electrode pole which collectively provide
        (a) a demarcated surface area lying between said disposed electrode poles on said exterior surface of said obturator,
        (b) a discrete gapped space which exists adjacent to and over said demarcated surface area between said disposed electrode poles as a cauterization zone, and
        (c) an on-demand electrode system for generating a direction-oriented and spatially-controlled flow of electrical arc current sufficient to coagulate and cauterize tissue in-vivo, and
        (d) direction-oriented coagulation cauterization of tissue from within the lumen of an occluded catheter in-vivo via said gapped space of said obturator; and
    electrical current conveyance apparatus which provides sufficient electric cower for tissue coagulation in-vivo, is contained internally at least within said proximal end section of said obturator, and is joined to each electrode spatially disposed on the surface of said obturator.

2. A complete bipolar coagulator suitable for passage through the lumen of a catheter and for in-vivo coagulation cauterization of tissue which is occluding at least one sidewall hole leading to the internal lumen of a catheter previously implanted into the body of a living subject for in-vivo flow release of fluids, said bipolar coagulator comprising:
    a sized flexible obturator of fixed dimensions and substantially cylindrical form which will fit within and pass through the inner diameter of the internal lumen of the catheter previously implanted in-vivo, said sized flexible obturator
        (i) having a shaped proximal end section able to pass within the inner diameter of the internal lumen of the implanted catheter, a distal end section, and a flexible body section able to pass through and around such internal lumen bends as exist within the implanted catheter, and
        (ii) being constituted at least in part of an electrically insulating material;
    at least two electrodes spatially disposed at different and direction-oriented positions on the exterior surface of said proximal end section of said flexible obturator, wherein each of said electrodes comprises a discrete electrode tip disposed on said exterior proximal end surface of said obturator at a pre-chosen position and an electrically communicating electrode body which is joined to said electrode tip and which extends into the interior of said obturator, and whereby said at least two direction-oriented disposed electrodes present at least one positively charged electrode pole and at least one negatively charged electrode pole which collectively Provide
        (a) a demarcated surface area lying between said disposed electrode poles on said exterior surface of said obturator, (b) a discrete gapped space which exists adjacent to and over said demarcated surface area between said disposed electrode poles as a cauterization zone, and (c) an on-demand electrode system for generating a direction-oriented and spatially-controlled flow of electrical arc current sufficient to coagulate and cauterize tissue in-vivo, and (d) direction-oriented coagulation cauterization of tissue from within the lumen of an occluded catheter in-vivo via said gapped space of said obturator;

electrical current conveyance apparatus which provides sufficient electric rower for tissue coagulation in-vivo, is contained internally at least within said proximal end section of said obturator, and is joined to each electrode spatially disposed on the surface of said obturator; and a source of electrical current in electrical flow communication with said electrical current conveyance apparatus.

3. A bipolar coagulator suitable for passage through the internal lumen of a catheter and for in-vivo coagulation cauterization of cranial tissue which is occluding at least one sidewall hole leading to the internal lumen of a ventricular catheter previously implanted into a cranial ventricle of a living subject for in-vivo flow release of cranial fluids, said bipolar coagulator comprising:

a sized flexible obturator of fixed dimensions and substantially cylindrical form which will fit within and pass through the inner diameter of the internal lumen of the ventricular catheter previously implanted in-vivo, said sized flexible obturator (i) having a shaped proximal end section able to pass within the inner diameter of the internal lumen of the implanted ventricular catheter, a distal end section, and a flexible body section able to pass through and around such internal lumen bends as may exist within the implanted ventricular catheter, and (ii) being constituted at least in part of an electrically insulating material;

at least two electrodes spatially disposed at different and direction-oriented positions on said exterior surface of said proximal end section of said flexible obturator, wherein each of said electrodes comprises a discrete electrode tip disposed on said exterior proximal end surface of said obturator at an individual pre-chosen position and an electrically communicating electrode body which is joined to said electrode tip and which extends into the interior of said obturator, and whereby said at least two direction-oriented disposed electrodes present at least one positively charged electrode pole and at least one negatively charged electrode pole which collectively provide (a) a demarcated surface area lying between said disposed electrode poles on said exterior surface of said obturator, (b) a discrete gapped space which exists adjacent to and over said demarcated surface area between said disposed electrode poles as a cauterization zone, and (c) an on-demand electrode system for generating a direction-oriented and spatially-controlled flow of electrical arc current sufficient to coagulate and cauterize tissue in-vivo, and (d) direction-oriented coagulation cauterization of tissue from within the lumen of an occluded catheter in-vivo via said gapped space of said obturator; and electrical current conveyance apparatus which provides sufficient electric power for tissue coagulation in-vivo, is contained internally at least within said proximal end section of said obturator, and is joined to each electrode spatially disposed on the surface of said obturator.

4. A complete bipolar coagulator suitable for passage through the internal lumen of a catheter and for in-vivo coagulation cauterization of cranial tissue which is occluding at least one sidewall hole leading to the internal lumen of a ventricular catheter previously implanted into a cranial ventricle of a living subject for in-vivo flow release of cranial fluids, said bipolar coagulator comprising:

a sized flexible obturator of fixed dimensions and substantially cylindrical form which will fit within and pass through the inner diameter of the internal lumen of the ventricular catheter previously implanted in-vivo, said sized flexible obturator (i) having a shaped proximal end section able to pass within the inner diameter of the internal lumen of the implanted ventricular catheter, a distal end section, and a flexible body section able to pass through and around such internal lumen bends as exist within the implanted ventricular catheter, and (ii) being constituted at least in part of an electrically insulating material;

at least two electrodes spatially disposed at different and direction-oriented positions on said exterior surface of said proximal end section of said flexible obturator, wherein each of said electrodes comprises a discrete electrode tip disposed on said exterior proximal end surface of said obturator at a pre-chosen position and an electrically communicating electrode body which is joined to said electrode tip and which extends into the interior of said obturator, and whereby said at least two direction-oriented disposed electrodes present at least one positively charged electrode pole and at least one negatively charged electrode pole which collectively provide (a) a demarcated surface area lying between said disposed electrode poles on said exterior surface of said obturator, (b) a discrete gapped space which exists adjacent to and over said demarcated surface area between said disposed electrode poles as a cauterization zone, and (c) an on-demand electrode system for generating a direction-oriented and spatially-controlled flow of electrical arc current sufficient to coagulate and cauterize tissue in-vivo, and (d) direction-oriented coagulation cauterization of tissue from within the lumen of an occluded catheter in-vivo via said gapped space of said obturator;

electrical current conveyance apparatus which provides sufficient electric power for tissue coagulation in-vivo, is contained internally at least within said proximal end section of said obturator, and is joined to each electrode spatially disposed on the surface of said obturator; and a source of electrical current in electrical flow communication with said electrical current conveyance apparatus.

5. The bipolar coagulator as recited in claim 1, 2, 3 or 4 wherein said obturator body further comprises at least one internal body cavity adjacent to said proximal end of said obturator.

6. The bipolar coagulator as recited in claim 1, 2, 3 or 4 further comprising a sensor apparatus disposed on the exterior surface of said proximal end section of said obturator.

7. A method for in-vivo coagulation cauterization of tissue which is occluding at least one sidewall hole leading to the internal lumen of a catheter previously implanted into the body of a living subject for in-vivo flow release of fluids, said method comprising:

obtaining a bipolar coagulator device comprising
  a flexible obturator of fixed dimensions and substantially cylindrical form which is configured to fit within and pass through the inner diameter of the internal lumen of the catheter previously implanted in-vivo, said flexible obturator
    (i) comprising a shaped proximal end section adapted for passage within the inner diameter of the internal lumen of the implanted catheter, a distal end section, and a flexible body section adapted for passage through and around such internal lumen bends as may exist within the implanted catheter, and
    (ii) being constituted at least in part of an electrically insulating material;
  at least two electrodes spatially disposed at different, direction-oriented, pre-chosen positions on the exterior surface of said proximal end section of said flexible obturator, each of said electrodes comprising a discrete electrode tip disposed on said exterior proximal end surface of said obturator at a pre-chosen position and an electrically communicating electrode body which is joined to said electrode tip and which extends into the interior of said obturator, said at least two direction-oriented disposed electrodes providing at least one positively charged electrode pole and at least one negatively charged electrode pole which collectively identify
    (a) a demarcated surface area lying between said disposed electrode poles on said exterior surface of said obturator,
    (b) a discrete gapped space which exists adjacent to and over said demarcated surface area between said disposed electrode poles as a cauterization zone, and
    (c) an on-demand electrode system for generating a direction-oriented and spatially-controlled flow of electrical arc current for coagulation cauterization over said gapped space of said obturator; and
  electrical current conveyance apparatus which is contained internally at least within said proximal end section of said obturator and is joined to each electrode spatially disposed on the surface of said obturator;
introducing said bipolar coagulator device into the internal lumen of the previously implanted catheter;
advancing said introduced bipolar coagulator device within the lumen of the previously implanted catheter until occluding tissue in-situ is encountered;
applying electrical current to said electrical current conveyance apparatus of said bipolar coagulator device; and
coagulating the occluding tissue in-situ using a direction-oriented and spatially controlled electric arc current generated by said bipolar coagulator device.

8. A method for in-vivo coagulation cauterization of cranial tissue which is occluding at least one sidewall hole leading to the internal lumen of a ventricular catheter previously implanted into a cranial ventricle of a living subject for in-vivo flow release of cranial fluids, said method comprising:

obtaining a bipolar coagulator device comprising
  a flexible obturator of fixed dimensions and substantially cylindrical form which is configured to fit within and pass through the inner diameter of the internal lumen of the catheter previously implanted in-vivo, said flexible obturator
    (i) comprising a shaped proximal end section adapted for passage within the inner diameter of the internal lumen of the implanted catheter, a distal end section, and a flexible body section adapted for passage through and around such internal lumen bends as may exist within the implanted catheter, and
    (ii) being constituted at least in part of an electrically insulating material;
  at least two electrodes spatially disposed at different, direction-oriented, pre-chosen positions on the exterior surface of said proximal end section of said flexible obturator, each of said electrodes comprising a discrete electrode tip disposed on said exterior proximal end surface of said obturator at a pre-chosen position and an electrically communicating electrode body which is joined to said electrode tip and which extends into the interior of said obturator, said at least two direction-oriented disposed electrodes providing at least one positively charged electrode pole and at least one negatively charged electrode pole which collectively identify
    (a) a demarcated surface area lying between said disposed electrode poles on said exterior surface of said obturator,
    (b) a discrete gapped space which exists adjacent to and over said demarcated surface area between said disposed electrode poles as a cauterization zone, and
    (c) an on-demand electrode system for generating a direction-oriented and spatially-controlled flow of electrical arc current for coagulation cauterization over said gapped space of said obturator; and
  electrical current conveyance apparatus which is contained internally at least within said proximal end section of said obturator and is joined to each electrode spatially disposed on the surface of said obturator;
introducing said bipolar coagulator device into the internal lumen of the previously implanted catheter;
advancing said introduced bipolar coagulator device within the internal lumen of the previously implanted ventricular catheter until occluding tissue in-situ is encountered;
applying electrical current to said electrical current conveyance apparatus of said bipolar coagulator device; and
coagulating the occluding tissue in-situ using a direction-oriented and spatially controlled electric arc current generated by said bipolar coagulator device.

* * * * *